(12) United States Patent
Roth et al.

(10) Patent No.: US 10,794,883 B2
(45) Date of Patent: Oct. 6, 2020

(54) COLORIMETRIC DETECTION OF ALUMINUM IN AN AQUEOUS SAMPLE

(71) Applicant: Hach Company, Loveland, CO (US)

(72) Inventors: Melanie Ann Roth, Loveland, CO (US); Angella NIcholle Greenawalt, Fort Collins, CO (US)

(73) Assignee: Hach Company, Loveland, CO (US)

( * ) Notice: Subject to any disclaimer, the term of this patent is extended or adjusted under 35 U.S.C. 154(b) by 21 days.

(21) Appl. No.: 16/277,397

(22) Filed: Feb. 15, 2019

(65) Prior Publication Data
US 2020/0264145 A1 Aug. 20, 2020

(51) Int. Cl.
G01N 31/22 (2006.01)
G01N 33/18 (2006.01)
G01N 21/31 (2006.01)

(52) U.S. Cl.
CPC ............. *G01N 31/22* (2013.01); *G01N 21/31* (2013.01); *G01N 33/1813* (2013.01); *G01N 33/1826* (2013.01)

(58) Field of Classification Search
CPC .... G01N 31/22; G01N 21/31; G01N 33/1813; G01N 33/1826
See application file for complete search history.

(56) References Cited

U.S. PATENT DOCUMENTS 4,533,642 A * 8/1985 Kelly ................. G01N 33/20
436/73
9,372,157 B1 * 6/2016 Todd .................. G01N 21/314

OTHER PUBLICATIONS

EJAC, Eurasian Journal of Analytical Chemistry, "A Simple Spectrophotornetrio Method for the Determination of Aluminum in Some Environmental, Biological, Soil and Pharmaceutical Samples Using 2-Hydroxynaphthaldehydebenzoylhydrazone", 1-15, 2010.
Dai Cheng et al., "Determination of Aluminum in Edible Jellyfish Using Chrome Azurol S with Spot Test on Filter Paper", Analytical Sciences, Feb. 2017, 6 pages, vol. 33, The Japan Society for Analytical Chemistry.
Hisham K. Fouad et al., "Development of spectrophotometric determination of beryllium in beryl minerals using chrome Azurol S", Arabian Journal of Chemistry, 2011, 6 pages, Elsevier B.V. on behalf of King Saud University.
Hach Company, "Method 10215", Jan. 2017, 6 pages, Edition 9, Hach Company.

* cited by examiner

*Primary Examiner* — Jamil Ahmed
(74) *Attorney, Agent, or Firm* — Ference & Associates LLC

(57) ABSTRACT

An embodiment provides a method for measuring aluminum concentration in an aqueous sample, including: preparing a chromeazurol S indicator solution; placing the chromeazurol S indicator solution in a sample containing aluminum, wherein the placing causes the chromeazurol S to chelate aluminum within the sample creating a colored complex; and measuring, using colorimetric techniques, a concentration of aluminum within the sample, wherein the measuring comprises measuring an absorbance at a wavelength for the colored complex. Other embodiments are described and claimed.

20 Claims, 3 Drawing Sheets

COLORIMETRIC DETECTION OF ALUMINUM IN AN AQUEOUS SAMPLE

FIELD

This application relates generally to water quality testing, and, more particularly, to measurement of aluminum within an aqueous sample.

BACKGROUND

The measurement of aluminum is important to ensure water quality. Applications for aluminum measurement may include waste water treatment, drinking water treatment, monitoring natural bodies of water, aqua farming, beverage/food manufacturing, pharmaceuticals, boiler systems, industrial processes, petrochemical processes, chemical tanks, or the like. Aluminum may be important for aquatic life and viability of natural bodies of water. Additionally, proper levels of aluminum may be necessary in manufacturing or processing operations such that reactions or processes within the operations properly occur. Proper measurement of aluminum may also be important to prevent interference of aluminum with a reaction in a solution.

Aluminum is an abundant metal in the earth's crust. Aluminum may leach from rock and/or soil into a water supply. Aluminum may also be introduced as aluminum hydroxide or aluminum sulfate in water treatment processes. Some studies have linked the presence of aluminum to dementia such as Alzheimer's disease. There are a number of methods to measure aluminum in drinking water. However, many aluminum tests require the minimization of possible interfering species for the test. Also, some aluminum detection tests are not accurate with regards to low concentrations of aluminum.

BRIEF SUMMARY

One embodiment provides a method for measuring aluminum concentration in an aqueous sample, comprising: preparing a chromeazurol S indicator solution; placing the chromeazurol S indicator solution in a sample containing aluminum, wherein the placing causes the chromeazurol S to chelate aluminum within the sample creating a colored complex; and measuring, using colorimetric techniques, a concentration of aluminum within the sample, wherein the measuring comprises measuring an absorbance at a wavelength for the colored complex.

Another embodiment provides a device for measuring a concentration of aluminum in an aqueous sample, comprising: a processor; a memory device that stores instructions executable by the processor to: introduce an aqueous sample to a reaction vessel; prepare a chromeazurol S indicator solution; place the chromeazurol S indicator solution in a sample containing aluminum, wherein the placing causes the chromeazurol S to chelate aluminum within the sample creating a colored complex; and measure, using colorimetric techniques, a concentration of aluminum within the sample, wherein the measuring comprises measuring an absorbance at a wavelength for the colored complex.

A further embodiment provides a measurement device for measuring aluminum concentration in an aqueous sample, comprising: a processor; a memory device that stores instructions executable by the processor to: receive, within the measurement device, a prepared chromeazurol S indicator solution; receive, within the measurement device, a sample containing aluminum, wherein the receiving causes the chromeazurol S to chelate aluminum within the sample creating a colored complex; and measure, using the measurement device and colorimetric techniques, a concentration of aluminum within the sample, wherein the measuring comprises measuring an absorbance at a wavelength for the colored complex.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
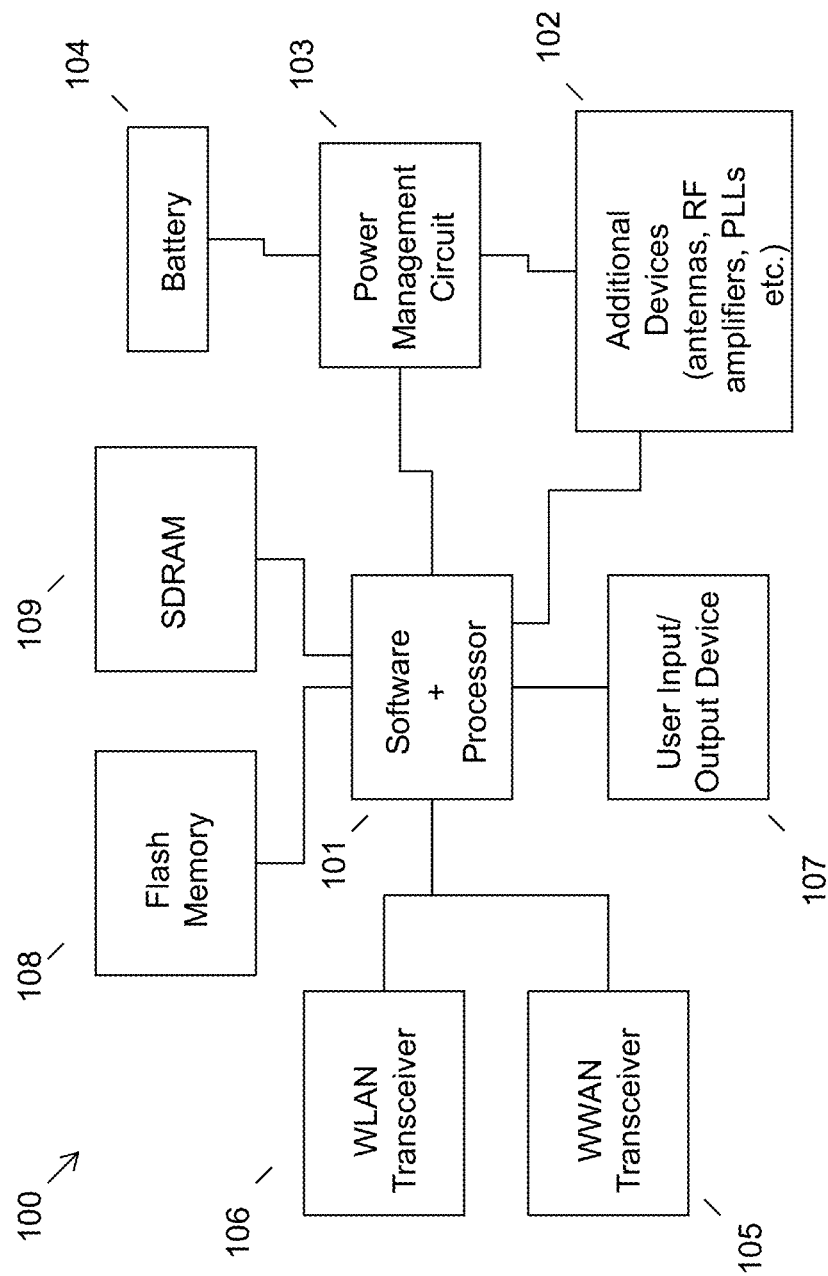
FIG. 1 illustrates an example of computer circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Colorimetric methods are commonly used to measure aluminum levels. One method includes the Hach Method 10215 test kit, using TNTplus™ 848. This method requires a recommended sample pH that is between 2.5 and 3.5. The method also requires the sample temperature to be at 20-23° C. Reagents for the method suggests storing reagents at 15-25° C. The method also requires 25 minutes of time to yield a measurement of aluminum, which is a significant length of time. Additionally, the method only measures a range of 0.020-0.5 parts per million (ppm) of aluminum. Thus, this method does not provide for measurement of lower aluminum concentrations or may provide inaccurate readings if the aluminum concentrations are too low. Additionally, samples are recommended to be stored at a pH of less than 2.0 for later analysis. The method requires careful pipetting and addition of reagents in addition to the 25 minute wait time for the reaction to complete. The method uses standard colorimetric techniques providing a measurement of aluminum in a sample typically as milligrams per liter. However, the colorimetric assay requires the use of a sample blank to be subtracted from the test result. Additionally, interfering ions may lead to inaccurate readings. These interfering ions include $Mg^{2+}$, $K^+$, $Na^+$, $NH_4^+$, $Cl^-$, $NO_3^-$, $SO_4^{2-}$, $ca^{2+}$, $Ag^+$, $Mn^{2+}$, $Cd^{2+}$, $CO^{2+}$, $Ni^{2+}$, $Sn^{2+}$, $Pb^{2+}$, $PO_4^{3-}$, $Cu^{2+}$, $Hg^{2+}$, $Fe^{2+}$, $Fe^{3+}$, $zn^{2+}$, $Si^{4+}$, $Cr^{3+}$, $Cr^{6+}$, and $F^-$.

Thus, the current aluminum testing methods have limitations which are overcome by the methods and techniques as described in more detail herein. One limitation of the current technique is that it requires a longer process than the methods described herein. Additionally, the traditional colorimetric methods require the preparation of a separate "blank" vial. The extra step of preparing a blank vial can introduce error to the measurement based upon individual human techniques in preparing the blank. Also, since the traditional colorimetric techniques are sensitive to a multitude of interferants, the presence of interfering ions may reduce the accuracy of content of a sample containing aluminum. Additionally, the methods described herein provide a larger range of aluminum detection beyond those of conventional techniques. Specifically, the described method and system provides for measurement of aluminum concentrations at lower concentrations than the traditional measurement techniques.

Accordingly, an embodiment includes preparation of a chromeazurol S indicator solution. Preparation of the chromeazurol S indicator solution may include preparing the chromeazurol S in a buffer solution. Chromeazurol S may also be referred to as Mordant Blue 29. In an embodiment, the buffer may contain an additive. For example, the buffer solution may contain acetate, succinic acid, sodium succinate, or the like. The buffer may facilitate the generation of a calibration curve, for example, succinic acid/sodium succinate buffer was used to generate the calibration curve of FIG. 3. However, this is a non-limiting example and other buffer solutions may be used. The buffer may be selected to maintain a pH at, around, below, or greater than pH 5.0. The buffer may also be selected as to not interfere with an analyte, such as aluminum. Additionally, the buffer solution may contain a surfactant. In an embodiment, the chromeazurol S indicator solution may be placed in an aqueous sample containing aluminum. The delivery method of reagents, for example, the chromeazurol S, to the aqueous sample, may be accomplished through pipetting, droppers, test strips, powder pillows, using a solid, using a liquid solution, or the like. In the presence of aluminum within the sample, the chromeazurol S may chelate the aluminum in the sample to create a colored complex. In an embodiment, colorimetric techniques may measure a concentration of the aluminum from the colored complex. For example, the measuring may be a measurement of an absorbance at a wavelength for the colored complex. The measuring may include taking a ratio of absorbance collected at multiple wavelengths. Different measurement devices may be used to perform the measurement, for example, a portable parallel analyzer (PPA, such as the SL1000 available from Hach Company, Loveland, Colo.), test strips, colorimetric analyzers, spectrophotometers, pocket colorimeters, online process instruments, and the like.

The illustrated example embodiments will be best understood by reference to the figures. The following description is intended only by way of example, and simply illustrates certain example embodiments.

While various other circuits, circuitry or components may be utilized in information handling devices, with regard to an instrument for aluminum measurement according to any one of the various embodiments described herein, an example is illustrated in FIG. 1. For example, the device circuitry as described in FIG. 1 may be used for communicating measurements to another device or may be used as the device for receiving measurements. Device circuitry 100 may include a measurement system on a chip design found, for example, a particular computing platform (e.g., mobile computing, desktop computing, etc.) Software and processor(s) are combined in a single chip 101. Processors comprise internal arithmetic units, registers, cache memory, busses, I/O ports, etc., as is well known in the art. Internal busses and the like depend on different vendors, but essentially all the peripheral devices (102) may attach to a single chip 101. The circuitry 100 combines the processor, memory control, and I/O controller hub all into a single chip 101. Also, systems 100 of this type do not typically use SATA or PCI or LPC. Common interfaces, for example, include SDIO and I2C.

There are power management chip(s) 103, e.g., a battery management unit, BMU, which manage power as supplied, for example, via a rechargeable battery 104, which may be recharged by a connection to a power source (not shown). In at least one design, a single chip, such as 101, is used to supply BIOS like functionality and DRAM memory.

System 100 typically includes one or more of a WWAN transceiver 105 and a WLAN transceiver 106 for connecting to various networks, such as telecommunications networks and wireless Internet devices, e.g., access points. Additionally, devices 102 are commonly included, e.g., a transmit and receive antenna, oscillators, RF amplifiers, PLLs, etc. System 100 includes input/output devices 107 for data input and display/rendering (e.g., a computing location located away from the single beam system that is easily accessible by a user). System 100 also typically includes various memory devices, for example flash memory 108 and SDRAM 109.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform aluminum measurement of an aqueous sample.

Figure 2:
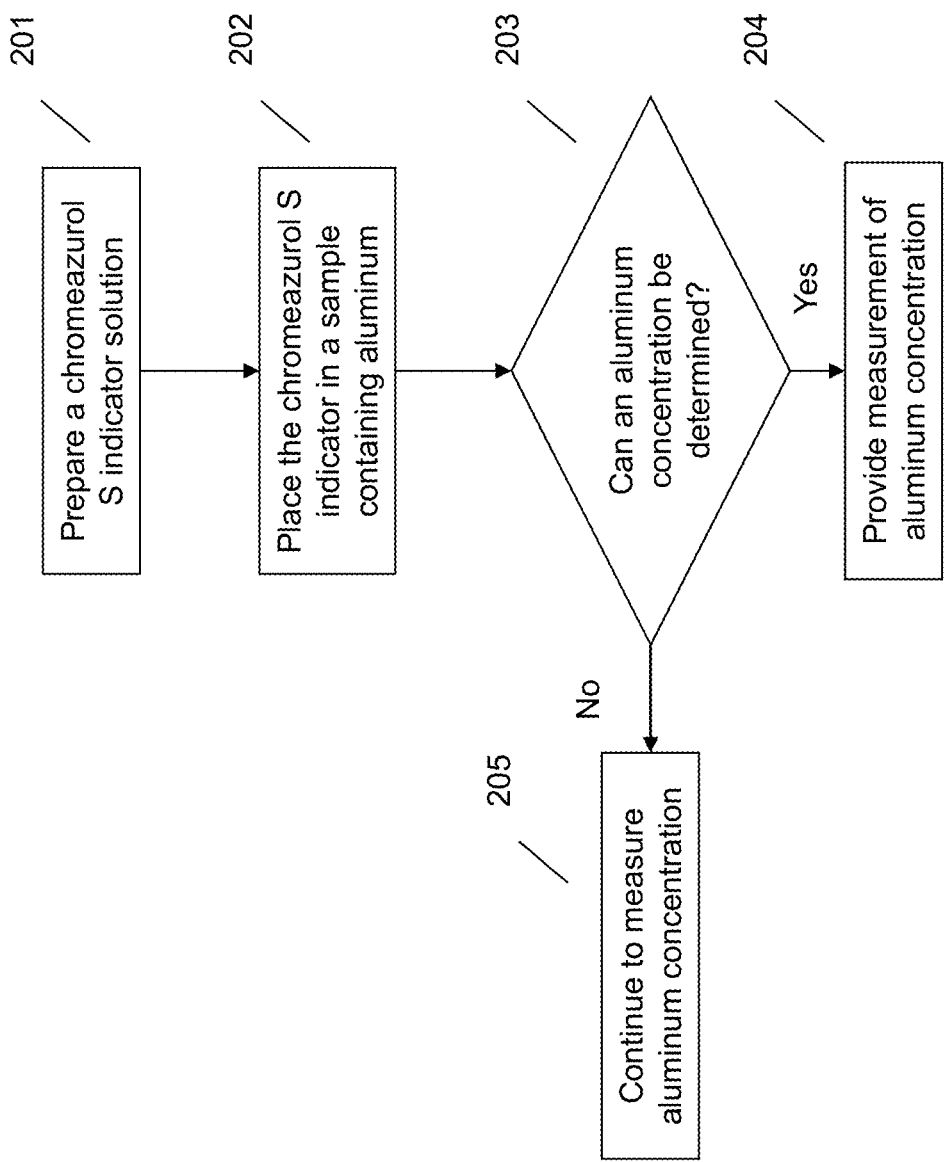
FIG. 2 illustrates an example flow diagram for aluminum detection using a measuring system.

Referring now to FIG. 2, an embodiment provides a measurement of an aluminum concentration in an aqueous environment. In an embodiment, a chromeazurol S indicator solution may be prepared. The chromeazurol S indicator solution may be placed in a sample, for example, an aqueous sample, that contains aluminum. The chromeazurol S may chelate aluminum within the sample. This chelating process may cause a colored complex to form. The resulting colored complex may be used to identify the concentration of aluminum within the sample. For example, using colorimetric techniques, parameters of the colored complex may be measured. For example, the colorimetric techniques may be used to measure the absorbance of the colored complex at one or more wavelengths. The absorbance may be proportional to an absorbance at a wavelength, the ratio of absorbance measured at multiple wavelengths, or the like.

At 201, in an embodiment a chromeazurol S indicator solution may be prepared. The chromeazurol S may be from a commercial source or synthesized in house. Unlike conventional techniques, the preparation of the indicator solution may be performed at, around, below, or greater than pH 5.0. Preparation of the indicator solution at, around, below, or greater than pH 5.0 may allow for a greater range of aluminum to be measured as compared to the conventional techniques. Preparation of the chromeazurol S indicator solution may include preparing the chromeazurol S in a buffer solution. The buffer components of the buffer solution may be selected based upon interaction with aluminum. In other words, the components may be selected in order to reduce interaction with aluminum. Additionally, the buffer components may be selected to chelate with interfering metals or the like that may be expected within the aqueous sample. In one embodiment, the buffer may contain acetate, or succinic acid. The buffer and/or indicator solution may additionally or alternatively contain an additive. The additive may contain a surfactant or alcohol. The surfactant may produce micelles in the solution. The wavelength maximum may shift as a result. The micelles, and subsequent wavelength shift, may be selected to utilize either an apparatus or condition that may require a shift in absorbance wavelength. For example, if a measurement device is tuned for a particular absorbance wavelength measurement, the surfactant may be added in order to produce a reaction that will result in an absorbance measurement that can be measured by the device.

At 202, the chromeazurol S indicator solution may be placed into a sample, for example, an aqueous sample. As an example, a user may want to measure an aluminum concentration in a natural water source (e.g., pond, lake, stream, etc.), in a residential water source (e.g., swimming pool, residential water supply, etc.), commercial or municipal water source (e.g., water treatment facility, water holding tank, facility water supply, laboratory sample, etc.), or the like. Thus, the chromeazurol S indicator solution may be placed or otherwise introduced to the aqueous sample. Different techniques for introducing the indicator solution to the aqueous sample may be utilized. For example, the sample may be placed in a vial, measurement device, vessel, or the like, and then the indicator solution may be introduced to the sample, for example, through use of a dropper, pipette, powder pillow, test strip, or the like. Alternatively, the indicator solution may be placed in a vial, measurement device, vessel, or the like, and the sample may thereafter be introduced to the indicator solution.

The sample may contain aluminum. The aluminum may be in a pure or compound form. Additionally or alternatively, the aluminum may be in a liquid form or a finely suspended form in the aqueous sample. In an embodiment, the aluminum sample and/or indicator solution may be added to a reaction vessel or other chamber of a measurement device. The introduction of the aluminum sample and/or indicator solution may be automated or manual. For example, a sample for testing may be pumped, aliquoted, pipetted, or introduced in any manner into a vessel or device. The aluminum for testing may be from any number of sources, for example, the aluminum may be from municipal water, drinking water, surface water, wastewater, industrial effluent, a natural waterway, a manufacturing process, swimming pool, or the like. The method and system may have more than one reaction vessel. For example, an aluminum sample may be introduced into a first vessel and subsequent steps of an embodiment may occur in another vessel or vessels. For example, the sample may be introduced into a first vessel or chamber, the indicator solution may be introduced into a second vessel or chamber, and then the sample and indicator solution may be mixed into a third vessel or chamber.

A chamber, vessel, cell, or the like, may contain an aqueous sample, chromeazurol S indicator solution, buffer, and associated reagents. A device may contain one or more bottles of reagents which contain necessary reagents such as, but not limited to, chromeazurol S indicator solution, buffers, or any reagent that may not be premixed before the measuring process. The regents contained in the one or more bottles may be pump fed or gravity fed. The flow of the reagents may be metered to ensure proper volume delivery to the measurement cell. The aqueous sample may be fed through a pressured inlet, a vessel, or the like. The aqueous sample may be introduced into the measurement chamber by a pump or gravity fed. The sampling device may be in series or parallel to an aqueous flow. The device may have a system to ensure proper mixing of the aqueous sample, chromeazurol S indicator solution, and related reagents.

The aqueous sample may include a sample from a natural body of water, a holding tank, a processing tank, a pipe, or the like. The aluminum containing sample may be in a continuous flow, a standing volume of liquid, or any combination thereof. In one embodiment, the aluminum containing sample may be introduced to a vessel, for example, a test chamber of the measurement device. Introduction of the aluminum containing sample into the measurement device may include placing or introducing the aluminum containing sample into a test chamber manually by a user or using a mechanical means, for example, gravity flow, a pump, pressure, fluid flow, or the like. For example, a water sample for aluminum testing may be introduced to a measurement or test chamber using a pump. In an embodiment, valves or the like may control the influx and efflux of the aqueous solution into or out of the one or more chambers, if present. In an embodiment, pumps, valves, and piping may control and direct the flow of reagents, for example, the indicator solution. In an embodiment, these systems may be automated or controlled by a processor.

Additionally or alternatively, the measurement device may be present within or introduced into a volume of the aluminum containing sample. The measurement device is then exposed to the volume of aqueous sample where it can perform measurements. For example, a handheld measurement device may include a test strip, test chip (such as Chemkeys available from Hach Company, Loveland, Colo.), or the like, that allows for dipping of the device or a portion of the device within the aqueous sample that then pulls a portion of the aqueous sample into the measurement device. As another example, the measurement device may be located within or in proximity to a water source or sample source and may periodically pull a sample for measurement. The system may be a flow-through system in which aluminum containing sample and/or reagents are automatically mixed and measured. Once the sample is in contact with the measurement system, the system may measure the aluminum in the sample using colorimetric techniques. In an embodiment, the measurement device may include one or more chambers in which the one or more method steps may be performed.

At 203, in an embodiment, the system may determine whether a concentration of aluminum within the sample can be determined or measured. To make this determination the system may attempt to measure a concentration of aluminum in the sample, for example, using one or more colorimetric techniques. In an embodiment, the indicator solution may include a colorimetric indicator and is sensitive to aluminum. Therefore, once introduced to a sample containing aluminum, the indicator solution, or components within the indicator solution, may react with the aluminum in the sample to create a colorimetric change in the sample. Specifically, when the indicator solution is introduced to the aqueous sample, the indicator, for example, chromeazurol S, may chelate the aluminum in the aqueous sample. This chelation causes a colorimetric change in the indicator solution. In other words, the chelation creates a colored complex that is of a different color than either the indicator solution alone, or the aqueous sample. In other words, the chelation causes a change in the absorbance wavelengths of the indicator solution and aqueous sample.

The colorimetric indicator may be water soluble. The colorimetric indicator may be chromeazurol S. The indicator may give a visual indication of aluminum concentration, which may be determined via absorbance measurements made using a laboratory apparatus or other measurement device. The resulting color or absorbance change from the interaction of the indicator with the aluminum in the sample may be determined photometrically, for example, using a spectrophotometer. For example, the measurement device may measure the absorbance wavelength of the colored complex. This absorbance wavelength may be proportional to a concentration of aluminum within the sample. Thus, by identifying the absorbance wavelength, the system can measure the concentration of aluminum in the sample. In one embodiment, two or more absorbance wavelengths may be measured. The aluminum concentration may then be proportional to the ratio of the multiple absorbance wavelengths. The absorbance intensity of the free chromeazurol S can also be monitored and used as an internal reference.

The concentration of aluminum may be determined in many ways. For example, comparison of a known concentration of aluminum with the indicator or absorbance wavelengths may be used to create a calibration curve of known aluminum concentrations. As another example, the absorbance of a sample containing aluminum may be determined using a set of known concentration aluminum samples to generate a calibration curve. The absorbance wavelengths of the resulting colored complex may also be compared to a "blank" to determine the concentration of aluminum within the sample.

Figure 3:
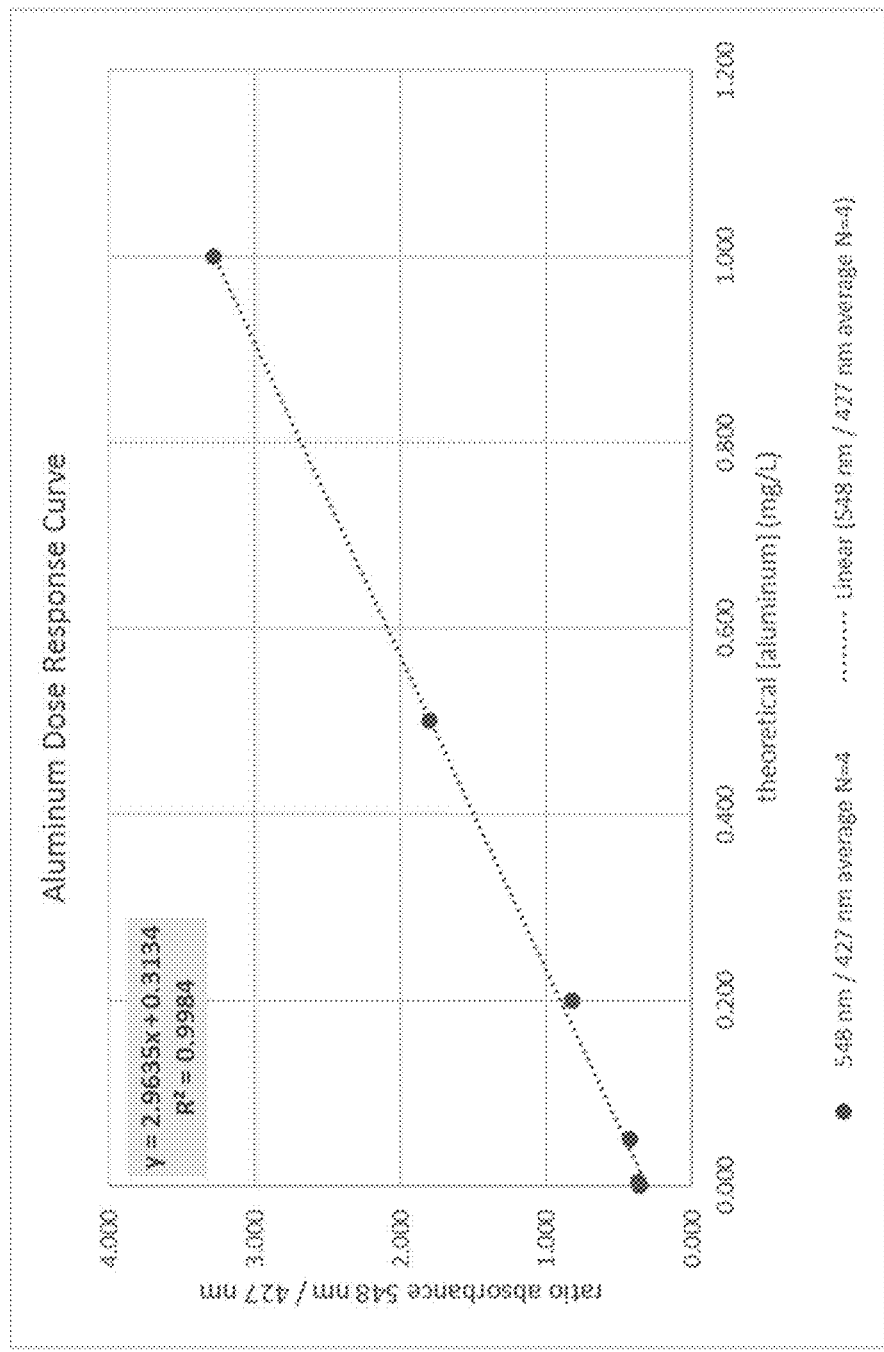
FIG. 3 illustrates an example embodiment of aluminum detection using a colorimetric technique.

Referring to FIG. 3, an example embodiment of determining an aluminum concentration within a sample using a colorimetric technique is illustrated. The described system or method may determine whether a colorimetric change occurred within the sample. Specifically, a colorimetric change may occur in the solution due to the existence of an aluminum concentration in the solution. In an embodiment, a ratio of absorbance may be taken. For example, a spectrophotometer may obtain absorbance at two wavelengths. In the example of FIG. 3, the two wavelengths are 548 nm and 427 nm. A ratio of these two wavelengths may be proportional to the aluminum concentration within the sample. Thus, the system may determine the aluminum concentration based upon the two wavelengths.

For example, the method described herein may chelate aluminum in the presence of the chromeazurol S indicator solution. For example, the chelation of aluminum may form a colored complex, and may result in a decrease of the absorbance intensity at 427 nm and an increase in absorption intensity at 548 nm. In this manner, the method may serve as its own control. A blank sample may not be required, although a blank may be prepared. A blank may be used for periodic calibration or testing. In an embodiment, a ratio absorbance may be plotted over a concentration of aluminum. In an embodiment, the reaction takes place quickly, therefore, the measurement of the concentration of aluminum is much quicker as compared to the conventional techniques. The detectable range of aluminum concentration may be dependent upon a calibration curve slope. A calibration curve may be optimized with a pathlength of a sample cell and/or instrument capabilities. The change in absorbance may be proportional to the aluminum concentration in a sample. Colorimetric measurement may be performed with standard laboratory equipment such as a spectrophotometer.

The determination may also be made based upon a predicted absorbance under known conditions. Predictions may be based upon variables such as temperature, pH, turbidity, pathlength, instrumentation, or the like. For example, the system may be programmed with a calibration curve. Deviations from the predicted curve may make results less reliable and cause the system to discontinue measuring or to send an alert. As another example, the system may receive information indicating a number of measurement cycles measuring aluminum concentration are outside acceptable limits. For example, such measurements may indicate that a step in the process may be suboptimal. Such steps may include aluminum chelation, indicator concentration, pH, temperature, or the like. At 205, in an embodiment, if a concentration of aluminum cannot be determined, the system may continue to measure aluminum, obtain another sample, attempt to chelate aluminum, or the like. Additionally or alternatively, the system may output an alarm, log an event, or the like.

If the concentration of aluminum can be determined at 203, the system may provide, at 204, the measurement of the aluminum concentration. The change in absorption may be measured using a spectrophotometer. Spectrophotometry is measurement of reflection or transmission properties of a sample measured at a given wavelength or set of wavelengths. Spectrophotometry may be a quantitative measure of how much light is absorbed by a material, for example, the colored complex resulting from the chelation of the aluminum by the indicator solution. For example, chromeazurol S in solution may be yellow/orange in color (427 nm), but the Aluminum-chromeazurol S complex may have an absorbance maximum around 548 nm. The change in absorption may also be measured using other colorimetric measurement devices.

Alternatively or additionally, aluminum concentration measurement may be at periodic intervals set by the user or preprogrammed frequencies in the device. Measurement of aluminum by a device allows for real time data with very little human involvement in the measurement process. Cleaning of the colorimetric chamber may be required at an unspecified time interval. A programmed calibration curve may be entered into the device.

The aluminum measurement may be an output upon a device in the form of a display, printing, storage, audio, haptic feedback, or the like. Alternatively or additionally, the output may be sent to another device through wired, wireless, fiber optic, Bluetooth®, near field communication, or the like. An embodiment may use an alarm to warn of an aluminum measurement or concentration outside acceptable levels. An embodiment may use a system to shut down water output or shunt water from sources with unacceptable levels of aluminum. For example, an aluminum measuring device may use a relay coupled to an electrically actuated valve, or the like.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring aluminum concentration in an aqueous sample, comprising:
preparing a chromeazurol S indicator solution;
placing the chromeazurol S indicator solution in a sample containing aluminum, wherein the placing causes the chromeazurol S to chelate aluminum within the sample creating a colored complex, wherein the sample comprises a homogeneous volume of fluid; and
measuring, using colorimetric techniques, a concentration of aluminum within the sample, wherein the measuring comprises measuring an absorbance at a wavelength for the colored complex and measuring an absorbance at a wavelength for the colored complex in the presence of the aluminum, wherein the concentration of aluminum is based upon a ratio of the absorbance at the wavelength for the colored complex and the absorbance at the wavelength for the colored complex in the presence of the aluminum.

2. The method of claim 1, wherein the measuring comprises measuring the absorbance intensity at two different wavelengths and creating a ratio of the two absorbance intensities to yield a ratio absorbance intensity.

3. The method of claim 2, wherein the ratio absorbance intensity is directly proportional to the concentration of aluminum within the sample and wherein the measuring comprises determining the concentration of aluminum based upon a calibration curve.

4. The method of claim 1, wherein the preparing comprises dissolving a chromeazurol S indicator in a buffered solution.

5. The method of claim 4, wherein the buffered solution comprises an additive selected from the group consisting of acetate and succinate.

6. The method of claim 4, wherein the dissolving comprises dissolving the chromeazurol S indicator in a buffered solution at a predetermined pH to maximize the desired wavelength intensities.

7. The method of claim 1, wherein the measuring comprises monitoring an absorbance intensity of free chromeazurol S of the indicator solution.

8. The method of claim 1, further comprising adding an additive, thereby shifting a wavelength of absorbance.

9. The method of claim 1, wherein the preparing comprises preparing the chromeazurol S within a measurement device selected from the group consisting of: a powder pillow, a test strip, and a liquid solution.

10. The method of claim 1, wherein the measuring comprises comparing the absorbance wavelength to an absorbance wavelength of a blank.

11. A device for measuring a concentration of aluminum in an aqueous sample, comprising:
a processor;
a memory device that stores instructions executable by the processor to:
prepare a chromeazurol S indicator solution;
place the chromeazurol S indicator solution in a sample containing aluminum, wherein the placing causes the chromeazurol S to chelate aluminum within the sample creating a colored complex, wherein the sample comprises a homogeneous volume of fluid; and
measure, using colorimetric techniques, a concentration of aluminum within the sample, wherein the measuring comprises measuring an absorbance at a wavelength for the colored complex and measuring an absorbance at a wavelength for the colored complex in the presence of the aluminum, wherein the concentration of aluminum is based upon a ratio of the absorbance at the wavelength for the colored complex and the absorbance at the wavelength for the colored complex in the presence of the aluminum.

12. The device of claim 11, wherein the measuring comprises measuring the absorbance intensity at two different wavelengths and creating a ratio of the two absorbance intensities to yield a ratio absorbance intensity.

13. The device of claim 12, wherein the ratio absorbance intensity is directly proportional to the concentration of aluminum within the sample and wherein the measuring comprises determining the concentration of aluminum based upon a calibration curve.

14. The device of claim 11, wherein the preparing comprises dissolving a chromeazurol S indicator in a buffered solution.

15. The device of claim 14, wherein the buffered solution comprises an additive selected from the group consisting of acetate and succinate.

16. The device of claim 14, wherein the dissolving comprises dissolving the chromeazurol S indicator in a buffered solution at a predetermined pH to maximize the desired wavelength intensities.

17. The device of claim 11, wherein the measuring comprises monitoring an absorbance intensity of free chromeazurol S of the indicator solution.

18. The device of claim 11, further comprising adding an additive, thereby shifting a wavelength of absorbance.

19. The method of claim 11, wherein the preparing comprises preparing the chromeazurol S within a measurement device selected from the group consisting of: a powder pillow, a test strip, and a liquid solution.

20. A measurement device for measuring aluminum concentration in an aqueous sample, comprising:
a processor;
a memory device that stores instructions executable by the processor to:
receive, within the measurement device, a prepared chromeazurol S indicator solution;
receive, within the measurement device, a sample containing aluminum, wherein the receiving causes the chromeazurol S to chelate aluminum within the sample creating a colored complex, wherein the sample comprises a homogeneous volume of fluid; and
measure, using the measurement device and colorimetric techniques, a concentration of aluminum within the sample, wherein the measuring comprises measuring an absorbance at a wavelength for the colored complex and measuring an absorbance at a wavelength for the colored complex in the presence of the aluminum, wherein the concentration of aluminum is based upon a ratio of the absorbance at the wavelength for the colored complex and the absorbance at the wavelength for the colored complex in the presence of the aluminum.

\* \* \* \* \*